United States Patent
Rezach

(10) Patent No.: US 9,949,763 B2
(45) Date of Patent: Apr. 24, 2018

(54) BONE FASTENER AND METHODS OF USE

(71) Applicant: Warsaw Orthopedic, Inc., Warsaw, IN (US)

(72) Inventor: William Alan Rezach, Atoka, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 429 days.

(21) Appl. No.: 14/303,836

(22) Filed: Jun. 13, 2014

(65) Prior Publication Data
US 2015/0359568 A1  Dec. 17, 2015

(51) Int. Cl.
*A61B 17/70* (2006.01)

(52) U.S. Cl.
CPC ........ *A61B 17/7032* (2013.01); *A61B 17/705* (2013.01); *A61B 17/7037* (2013.01)

(58) Field of Classification Search
CPC .............. A61B 17/7032; A61B 17/705; A61B 17/7037
See application file for complete search history.

(56) References Cited

U.S. PATENT DOCUMENTS

| | | | | |
|---|---|---|---|---|
| 6,206,879 B1 * | 3/2001 | Marnay | ............. | A61B 17/7035 606/53 |
| 7,803,174 B2 * | 9/2010 | Denis | ................ | A61B 17/7035 606/250 |
| 7,942,907 B2 * | 5/2011 | Richelsoph | ........ | A61B 17/7014 606/257 |
| 8,034,085 B2 * | 10/2011 | Slivka | ................ | A61B 17/7022 606/266 |
| 8,672,983 B2 * | 3/2014 | Biscup | .............. | A61B 17/7007 606/267 |
| 9,101,403 B2 * | 8/2015 | Biedermann | ...... | A61B 17/7032 |
| 9,241,739 B2 * | 1/2016 | Mueller | .............. | A61B 17/704 |
| 2002/0193795 A1 * | 12/2002 | Gertzbein | .......... | A61B 17/7041 606/269 |
| 2004/0039388 A1 * | 2/2004 | Biedermann | ...... | A61B 17/6433 606/71 |
| 2004/0111088 A1 * | 6/2004 | Picetti | ................ | A61B 17/7001 606/265 |
| 2005/0171537 A1 * | 8/2005 | Mazel | ................ | A61B 17/7037 606/264 |
| 2006/0074419 A1 * | 4/2006 | Taylor | ................ | A61B 17/7007 606/70 |
| 2008/0269810 A1 * | 10/2008 | Zhang | ................ | A61B 17/7001 606/305 |
| 2009/0131982 A1 * | 5/2009 | Schwab | ............. | A61B 17/7001 606/246 |
| 2010/0087865 A1 * | 4/2010 | Biedermann | ...... | A61B 17/7037 606/264 |
| 2011/0004251 A1 * | 1/2011 | Sweeney | ............ | A61B 17/1671 606/264 |
| 2014/0236238 A1 * | 8/2014 | Ark | .................... | A61B 17/7037 606/278 |

* cited by examiner

Primary Examiner — Ellen C Hammond

(57) ABSTRACT

A spinal implant comprises a first member including a surface that extends between a first portion and a second portion. The first member defines a first implant cavity adjacent the first portion and a second implant cavity adjacent the second portion. The first implant cavity is spaced from the second implant cavity. The surface defines a medial cavity. A second member is movable relative to the first member. The second member includes a first end aligned with the medial cavity and a second end configured to penetrate tissue. Systems and methods are disclosed.

20 Claims, 10 Drawing Sheets

BONE FASTENER AND METHODS OF USE

TECHNICAL FIELD

The present disclosure generally relates to medical devices for the treatment of spinal disorders, and more particularly to a surgical implant system including a bone fastener that provides stabilization while reducing stress on spinal elements.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. The rods may be attached via the fasteners to the exterior of two or more vertebral members. This disclosure describes an improvement over these prior art technologies.

SUMMARY

In one embodiment, a spinal implant is provided. The spinal implant comprises a first member including a surface that extends between a first portion and a second portion. The first member defines a first implant cavity adjacent the first portion and a second implant cavity adjacent the second portion. The first implant cavity is spaced from the second implant cavity. The surface defines a medial cavity. A second member is movable relative to the first member. The second member includes a first end aligned with the medial cavity and a second end configured to penetrate tissue. In some embodiments, systems and methods are disclosed.

BRIEF DESCRIPTION OF THE DRAWINGS

The present disclosure will become more readily apparent from the specific description accompanied by the following drawings, in which.

DETAILED DESCRIPTION

Figure 1:
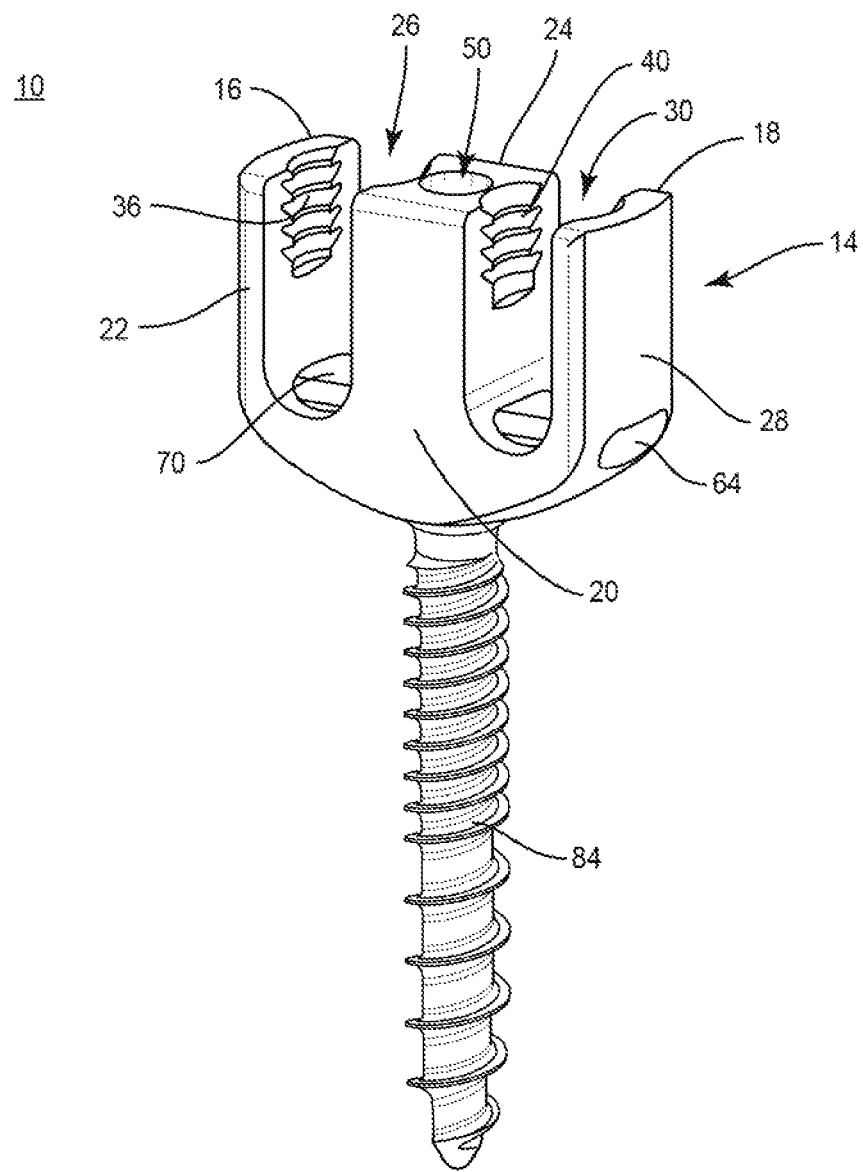
FIG. 1 is a perspective view of components of one embodiment of a spinal implant system in accordance with the principles of the present disclosure.

The exemplary embodiments of a surgical system and related methods of use disclosed are discussed in terms of medical devices for the treatment of musculoskeletal disorders and more particularly, in terms of a spinal implant system including a bone fastener. In some embodiments, the spinal implant system includes a bone fastener that can be employed with one or a plurality of spinal rods. In some embodiments, the spinal implant system includes a bone fastener comprising a proximal end that seats one or a plurality of spinal rods and a distal end including a shaft that penetrates tissue.

In one embodiment, the system includes a bone fastener including a dual headed multi-axial bone screw. In some embodiments, the bone fastener can be employed with surgical procedures, such as, for example, a pedicle subtraction osteotomy (PSO) and/or a vertebral column resection (VCR). In some embodiments, the bone fastener can be connected with one or a plurality of spinal rods, such as, for example, three spinal rods over a surgical site for a PSO and/or VCR procedure to prevent rod failures.

In some embodiments, the bone fastener includes a multi-axial configuration. In one embodiment, the bone fastener includes a center hole configured for disposal of a driver such that the driver mates with a bone screw shaft of the bone fastener. In one embodiment, the bone fastener includes a bone screw shaft positioned offset from a head of the bone fastener. The configuration of one or more components of the bone fastener facilitates placement of a plurality of spinal rods close together so that the driver does not have to be manipulated between inside faces of spaced arms of the head. In some embodiments, the head can be positioned inferior or superior to the bone screw shaft. In one embodiment, the head includes an overlap portion configured to prevent a crown of the bone fastener from exiting the head.

In some embodiments, the bone fastener includes a plurality of heads diagonally placed about the bone fastener and/or the bone screw head. This configuration of one or more components of the bone fastener facilitates a rocker instrument and/or counter torque being employed with the bone fastener. In one embodiment, the diagonal placement can include a left and/or right design to alter medial and/or lateral placement for a superior and/or inferior mis-match of spinal rods.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed spinal implant system may be alternatively employed in a surgical treatment with a patient in a prone or supine position, and/or employ various surgical approaches to the spine, including anterior, posterior, posterior mid-line, direct lateral, postero-lateral, and/or antero lateral approaches, and in other body regions. The present disclosure may also be alternatively employed with procedures for treating the lumbar, cervical, thoracic, sacral and pelvic regions of a spinal column. The spinal implant system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about" it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro-discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

Figure 2:
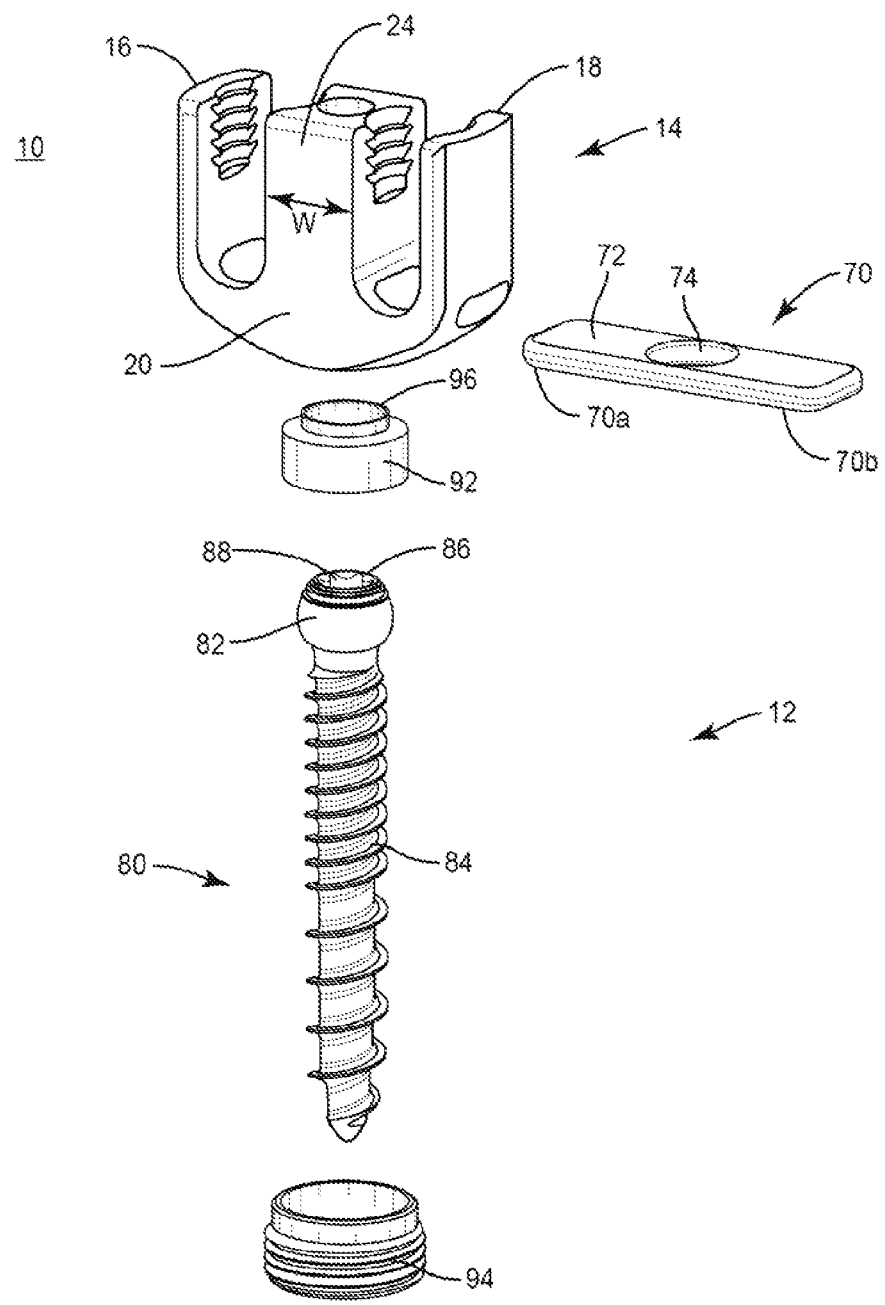
FIG. 2 is a perspective view of the components shown in FIG. 1 with parts separated.
Figure 3:
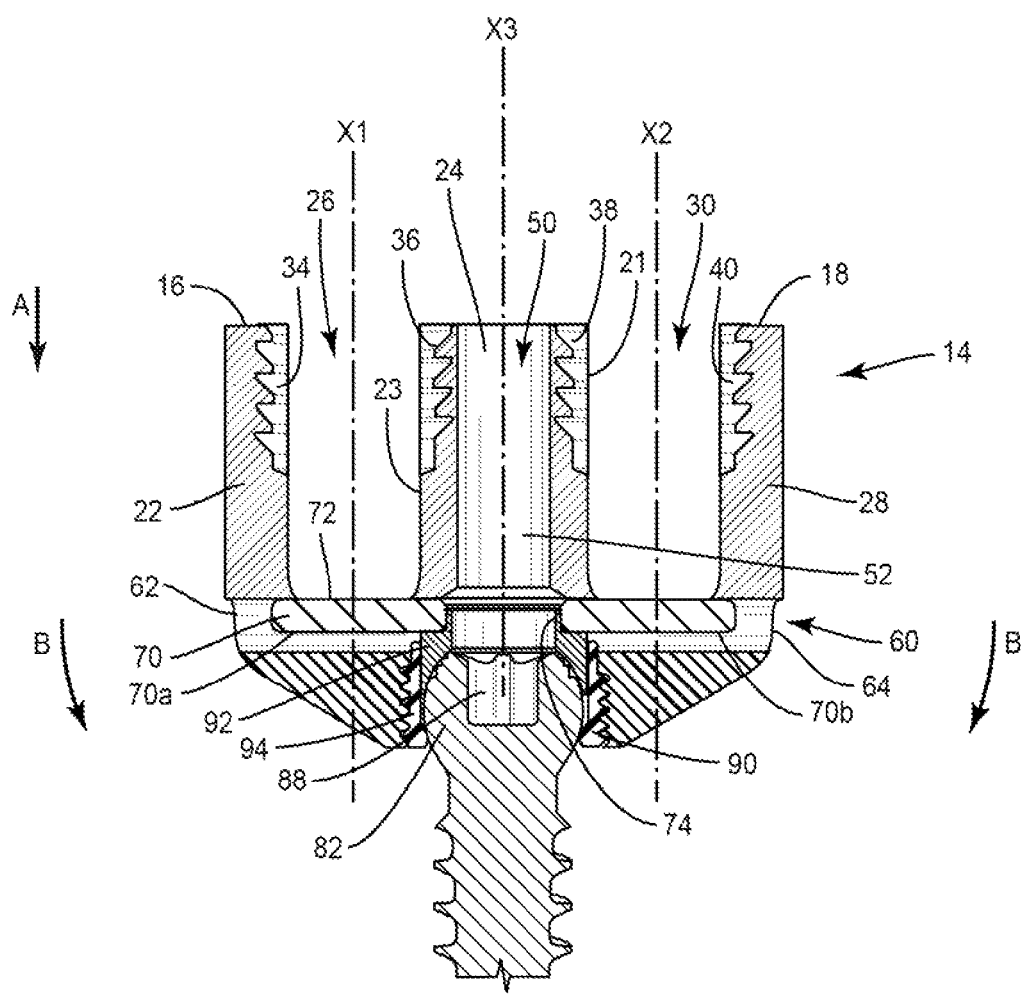
FIG. 3 is cross section view of the components shown in FIG. 1.

The following discussion includes a description of a surgical system including a bone fastener, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-3, there are illustrated components of a spinal implant system 10 including a spinal implant, such as, for example, a bone fastener 12.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Fastener 12 includes a member, such as, for example, a receiver 14. Receiver 14 includes a portion, such as, for example, an end 16 and a portion, such as, for example, an end 18. Receiver 14 includes a surface 20 that extends between ends 16, 18. In some embodiments, all or only a portion of surface 20 may have alternate surface configurations such as, for example, rough, arcuate, undulating, mesh, porous, semi-porous, dimpled and/or textured.

Figure 4:
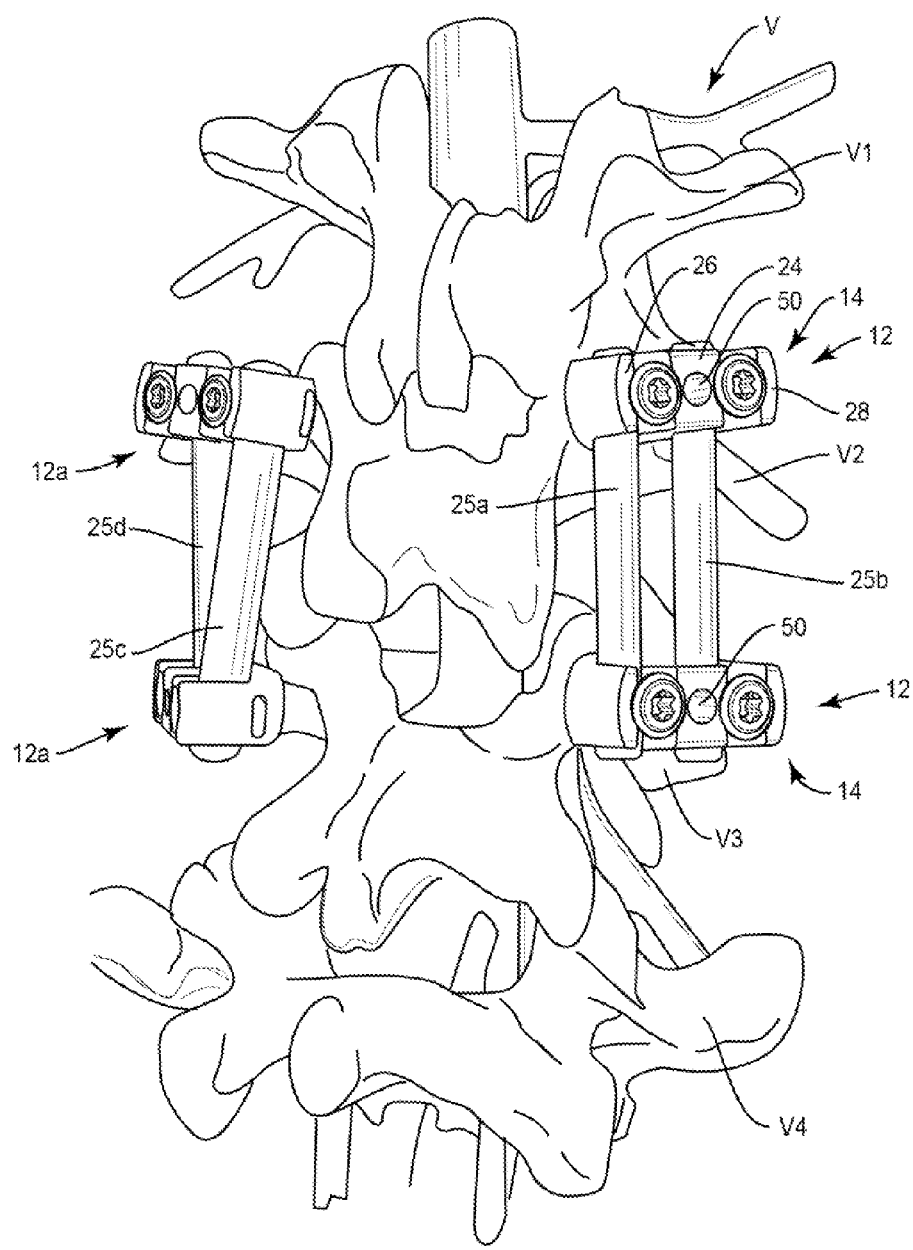
FIG. 4 is a perspective view of components of one embodiment of a spinal implant system in accordance with the principles of the present disclosure disposed with vertebrae.

End 16 includes an arm 22 and a wall surface 23 of a central arm 24 of receiver 14. Arm 22 and wall surface 23 are spaced apart to define a U-shaped implant cavity 26 therebetween, which is configured for disposal of a spinal implant, such as, for example, a spinal rod 25*a* (FIG. 4). Cavity 26 defines an axis X1, as shown in FIG. 3. In some embodiments, all or a portion of arm 22, wall surface 23 and/or cavity 26 can be disposed at alternate orientations relative to axis X1, such as, for example, transverse, perpendicular and/or other angular orientations such as acute or obtuse and/or may be offset or staggered.

Cavity 26 is substantially cylindrical in cross section. In some embodiments, all or only a portion of cavity 26 may have alternate cross section configurations, such as, for example, V-shaped, oval, oblong triangular, square, polygonal, irregular, uniform, non-uniform, offset, staggered and/or tapered. End 16 includes an inner surface 34, which comprises a portion of arm 22 and wall surface 23. Surface 34 includes a thread form 36 disposed along a portion of arm 22 and wall surface 23. Thread form 36 is configured for engagement with a coupling member, such as, for example, a setscrew (not shown) to retain spinal rod 25*a* within cavity 26. In some embodiments, surface 34 may be disposed with the coupling member in alternate fixation configurations, such as, for example, friction fit, pressure fit, locking protrusion/recess, locking keyway and/or adhesive.

End 18 includes an arm 28 and a wall surface 21 of arm 24. Arm 28 and wall surface 21 are spaced apart to define a U-shaped implant cavity 30 therebetween, which is configured for disposal of a spinal implant, such as, for example, a spinal rod 25*b* (FIG. 4). Cavity 30 defines an axis X2, as shown in FIG. 3, extending parallel to axis X1. Cavity 30 is disposed in spaced apart relation and adjacent cavity 22. In some embodiments, all or a portion of arm 28, wall surface 21 and/or cavity 30 can be disposed at alternate orientations relative to axis X2, such as, for example, transverse, perpendicular and/or other angular orientations such as acute or obtuse, coaxial and/or may be offset or staggered.

Cavity 30 is substantially cylindrical in cross section. In some embodiments, all or only a portion of cavity 30 may have alternate cross section configurations, such as, for example, V-shaped, oval, oblong triangular, square, polygonal, irregular, uniform, non-uniform, offset, staggered and/or tapered. End 18 includes an inner surface 38, which comprises a portion of arm 28 and wall surface 21. Surface 38 includes a thread form 40 disposed along a portion of arm 28 and wall surface 21. Thread form 40 is configured for engagement with a coupling member, such as, for example, a setscrew (not shown) to retain spinal rod 25*b* within cavity 30. In some embodiments, surface 38 may be disposed with the coupling member in alternate fixation configurations, such as, for example, friction fit, pressure fit, locking protrusion/recess, locking keyway and/or adhesive.

Arm 24 defines a medial cavity such as, for example, an elongated axial passageway 50. Passageway 50 includes a width w sized for passage of a surgical tool and/or for access to a member, such as, for example, screw 80, as described herein. Passageway 50 defines a central axis X3. Axis X3 is disposed in parallel orientation relative to axes X1, X2. In some embodiments, axis X3 may be disposed at alternate orientations, relative to axis X1 and/or X2, such as, for example, transverse, perpendicular and/or other angular orientations such as acute or obtuse and/or may be offset or staggered.

Receiver 14 includes a passageway 60 disposed perpendicular to axes X1, X2, X3. In some embodiments, passageway 60 may be disposed at alternate orientations relative to axis X1, X2 and/or X3, such as, for example, transverse, and/or other angular orientations such as acute or obtuse, coaxial and/or may be offset or staggered. As shown in FIG. 3, passageway 60 extends along a bottom portion of receiver 14 in communication with cavity 22 and cavity 30. Passageway 60 includes an opening 62 disposed with portion 16 and an opening 64 disposed with portion 18 configured to receive a part, such as, for example, an insert 70.

Insert 70 is configured for disposal in passageway 60 and perpendicular to axes X1, X2, X3. In some embodiments, insert 70 may be configured such that all or a portion of insert 70 is disposed at alternate orientations relative to axis X1, X2 and/or X3, such as, for example, transverse, and/or other angular orientations such as acute or obtuse, coaxial and/or may be offset or staggered.

Insert 70 includes a part 70*a*, a part 70*b* and an outer surface 72. Within passageway 60, insert 70 communicates with cavity 26 and cavity 30 such that surface 72 is engageable with spinal implants disposed therein, such as, for example, rods 25*a*, 25*b*. In some embodiments, all or only a portion of surface 72 may have alternate surface configurations such as, for example, rough, arcuate, undulating, mesh, porous, semi-porous, dimpled and/or textured.

Surface 72 defines a central opening 74 disposed between parts 70*a*, 70*b*. Part 70*a* is configured for disposal in cavity 26 and engagement with spinal rod 25*a*. Part 70*b* is configured for disposal in cavity 30 and engagement with spinal rod 25*b*. In one embodiment, opening 74 is aligned with passageway 50 for passage of a surgical tool and/or for access to screw 80, as described herein. In some embodiments, parts 70*a* and/or 70*b* can extend from opening 74 in alternate orientations, such as, for example, transverse and/or other angular orientations such as acute or obtuse and/or may be offset or staggered. In one embodiment, opening 74 and/or surface 72 defining opening 74 is configured for engagement and/or disposal of a crown assembly 90, as described herein. In some embodiments, insert 70 is configured to fix a selected orientation of screw 80 relative to receiver 14, as described herein.

In some embodiments, insert 70 can include a flexible configuration. In some embodiments, all or only a portion of insert 70 may have a semi-rigid, rigid, flexible or elastic configuration, and/or have elastic and/or flexible properties such as the elastic and/or flexible properties of the material examples described above. As such, insert 70 can provide a selective amount of deformation in an axial direction to engage screw 80, as described herein. In some embodiments, insert 70 may be compressible in an axial direction. In some embodiments, insert 70 can include a plurality of separately attachable or connectable portions or sections or may be monolithically formed as a single continuous element.

Fastener 12 includes screw 80, which includes an end, such as, for example, a head 82 and an end, such as, for example, a threaded shaft 84 configured to penetrate tissue. Head 82 is configured for alignment with passageway 50 to provide access for a surgical tool with screw 80. Head 82 includes a surface 86 that defines a socket 88 configured for engagement with a surgical tool via passageway 50. Socket 88 includes a hexalobe geometry configured for disposal of a similarly shaped bit of a tool, such as, for example, a driver. The driver engages the surfaces of socket 88 to rotate screw 80 relative to and about axis X3. Socket 88 is in communication with passageway 50 such that a driver may be inserted in passageway 50 and translated axially until the bit of the driver is disposed in socket 88. In some embodiments, socket 88 has a cruciform, phillips, square, hexagonal, polygonal, star or hexalobe cross sectional configuration for disposal of a correspondingly shaped portion of a driver.

Screw 80 is moveable along a plurality of axes relative to receiver 14 in a multi-axial configuration. In some embodiments, shaft 84 is selectively movable relative to receiver 14 and/or axis X3 through an angular range and disposable at a selected angle relative to receiver 14 and/or axis X3. In some embodiments, shaft 84 is selectively movable relative to receiver 14 and/or axis X3 through an angular range of 0-180 degrees.

Head 82 is configured for attachment to receiver 14 via crown assembly 90. Crown assembly 90 includes a crown 92 and a retainer 94. Crown 92 is aligned with passageways 50, 60 and includes a lip 96 that mates with surface 72. Lip 96 is disposed in opening 74 such that crown 92 is mated with insert 70. Head 82 is disposed in a contacting engagement with an inner concave surface of crown 92. The outer surface of head 82 is engageable with the inner surface of crown 92 to facilitate fixation of shaft 84 in a selected orientation of screw 80 relative to receiver 14. In some embodiments, all or only a portion of the outer surface of head 82 and/or the inner surface of crown 92 may have alternate surface configurations to enhance fixation of the surfaces, such as, for example, rough, arcuate, undulating, mesh, porous, semi-porous, dimpled and/or textured.

Retainer 94 is configured for disposal about crown 92 and head 82 to assemble screw 80 and crown assembly 90 with receiver 14. Retainer 94 includes an outer thread form that is engaged with an inner thread form of receiver 14. Retainer 94 is threaded with receiver 14 to capture and draw head 82 together with the components of crown assembly 90 to movably fix screw 80 with receiver 14. As such, screw 80 is moveable relative to receiver 14 in a multi-axial configuration and shaft 84 is selectively movable relative to receiver 14 and/or axis X3 through an angular range and disposable at a selected angle relative to receiver 14 and/or axis X3.

Insert 70 is configured to fix a selected orientation of screw 80 relative to receiver 14. In some embodiments, implants, such as, for example, spinal rods 25a, 25b contact surface 72 such that an axial force is applied to parts 70a, 70b, as shown by arrow A in FIG. 3. Parts 70a, 70b are driven and translate, in the direction shown by arrow A, and/or rotate, in the direction shown by arrows B, into engagement with crown 92 and/or retainer 94. As such, the axial force is applied to one or more components of crown assembly 90 and/or head 82 to fix a selected orientation of screw 80 relative to receiver 14, as described herein.

In assembly, operation and use, spinal implant system 10, similar to the systems and methods described herein, includes one or more fasteners 12 and is employed with a surgical procedure, such as, for example, a method for correction of deformities such as kyphosis or scoliosis, and/or a method for treating a patient with a PSO or a VCR. In some embodiments, one or all of the components of system 10 can be delivered or utilized as a pre-assembled device or can be assembled in situ.

As shown in FIG. 4, one or all of the components of system 10 can be employed with a surgical correction treatment of an applicable condition or injury of an affected section or sections of a spinal column, such as, for example, vertebrae V, which includes a plurality of vertebra V1-V4, and adjacent areas within a body. In use, to treat vertebrae V, a medical practitioner obtains access to a surgical site including vertebra V1-V4 in any appropriate manner, such as through incision and retraction of tissues. In some embodiments, one or all of the components of system 10 can be used in any existing surgical method or technique including open surgery, mini-open surgery, minimally invasive surgery and percutaneous surgical implantation, whereby a section of vertebrae V including vertebra V1-V4 are accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of system 10. A preparation instrument (not shown) can be employed to prepare tissue surfaces of vertebrae V, as well as for aspiration and irrigation of a surgical region.

Pilot holes are made in selected vertebra of vertebrae V2, V3 for receiving bone fasteners 12 assembled with receivers 14, screws 80 and inserts 70, as described herein. A surgical tool, such as, for example, a driver (not shown) is translated, in the direction shown by arrow A in FIG. 3, until a bit of the driver is disposed in socket 88. For each fastener 12, the driver is rotated causing fastener 12 to translate axially within a pilot hole such that shaft 84 is threaded and engaged with tissue. In some embodiments, the driver is removed from fastener 12.

Insert 70 is disposed with passageway 60 such that opening 74 is aligned with passageway 50. Surface 72 is disposed in cavities 26, 30 for engagement with spinal rods 25a, 25b. Spinal rods 25a, 25b are delivered to the surgical site and disposed with cavities 26, 30 of fasteners 12. Set screws are threaded with thread forms 36, 38 to fix spinal rods 25a, 25b with receiver 14.

The set screws apply a force to spinal rods 25a, 25b, in the direction shown by arrow A in FIG. 3, such that spinal rods 25a, 25b apply an axial force to parts 70a, 70b. Parts 70a, 70b are driven and translate, in the direction shown by arrow A, and/or rotate, in the direction shown by arrows B, into engagement with crown 92 and/or retainer 94. As such, the axial force is applied to one or more components of crown assembly 90 to fix a selected orientation of screw 80 relative to receiver 14, as described herein.

In some embodiments, as shown in FIG. 4, spinal correction system 10 comprises a bilateral spinal construct. The bilateral spinal construct comprises a first set of bone fasteners 12 attached with rods 25a. 25b and connected with a lateral portion of vertebrae V, as described above. The bilateral spinal construct also comprises a second set of fasteners 12a, similar to fasteners 12 described herein, and attached with spinal rods 25c, 25d, similar to rods 25a, 25b described herein, and similarity connected with a contralateral portion of vertebrae V.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10. In some embodiments, system 10 may include one or a plurality of rods, plates, connectors and/or bone fasteners for use with a single vertebral level or a plurality of vertebral levels.

In some embodiments, one or more of fasteners 12 may be engaged with tissue in various orientations, such as, for example, series, parallel, offset, staggered and/or alternate vertebral levels. In some embodiments, one or more of fasteners 12 may comprise multi-axial screws, sagittal angulation screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In one embodiment, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

Figure 5:
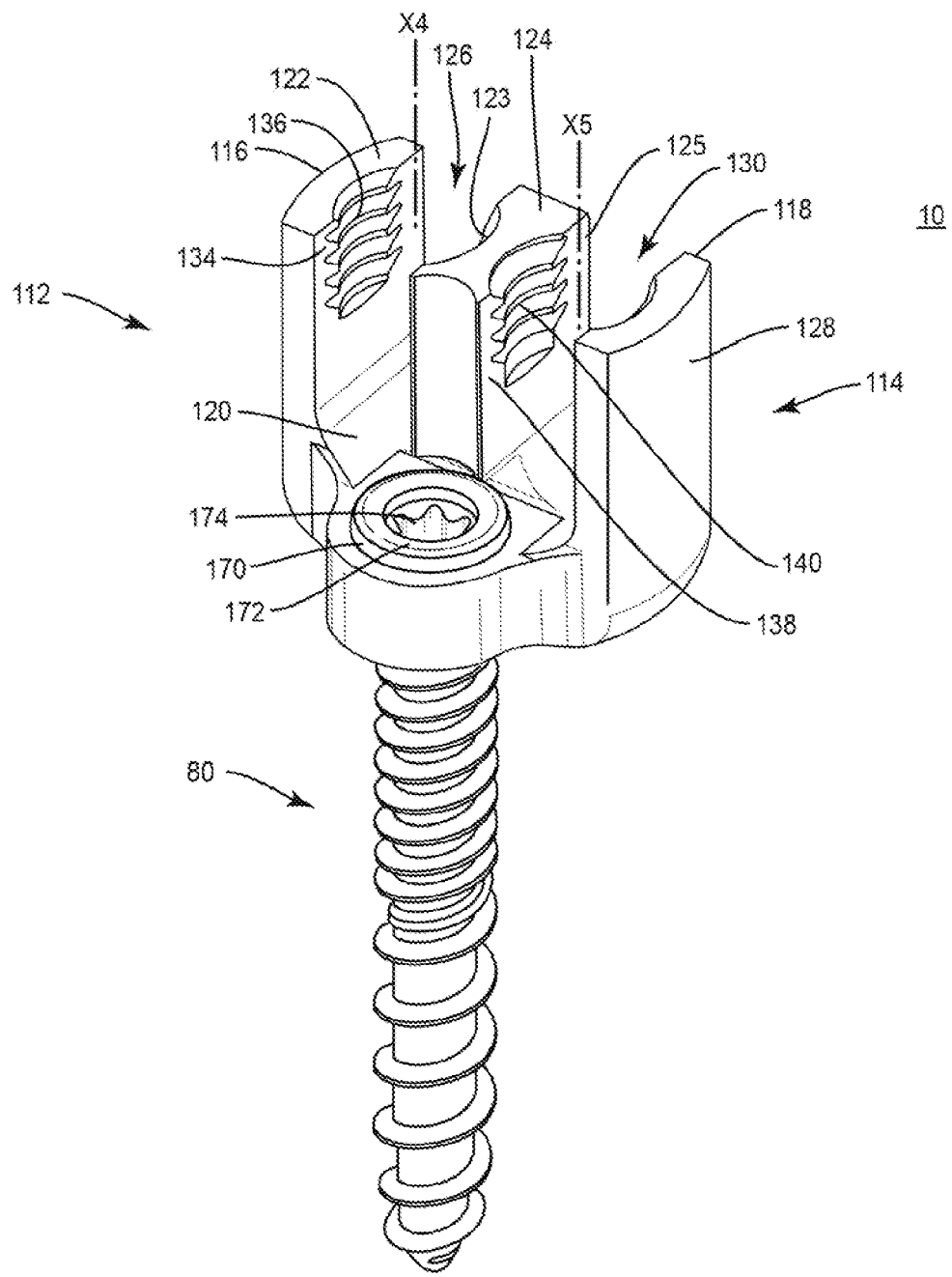
FIG. 5 is a perspective view of components of one embodiment of a spinal implant system in accordance with the principles of the present disclosure.
Figure 6:
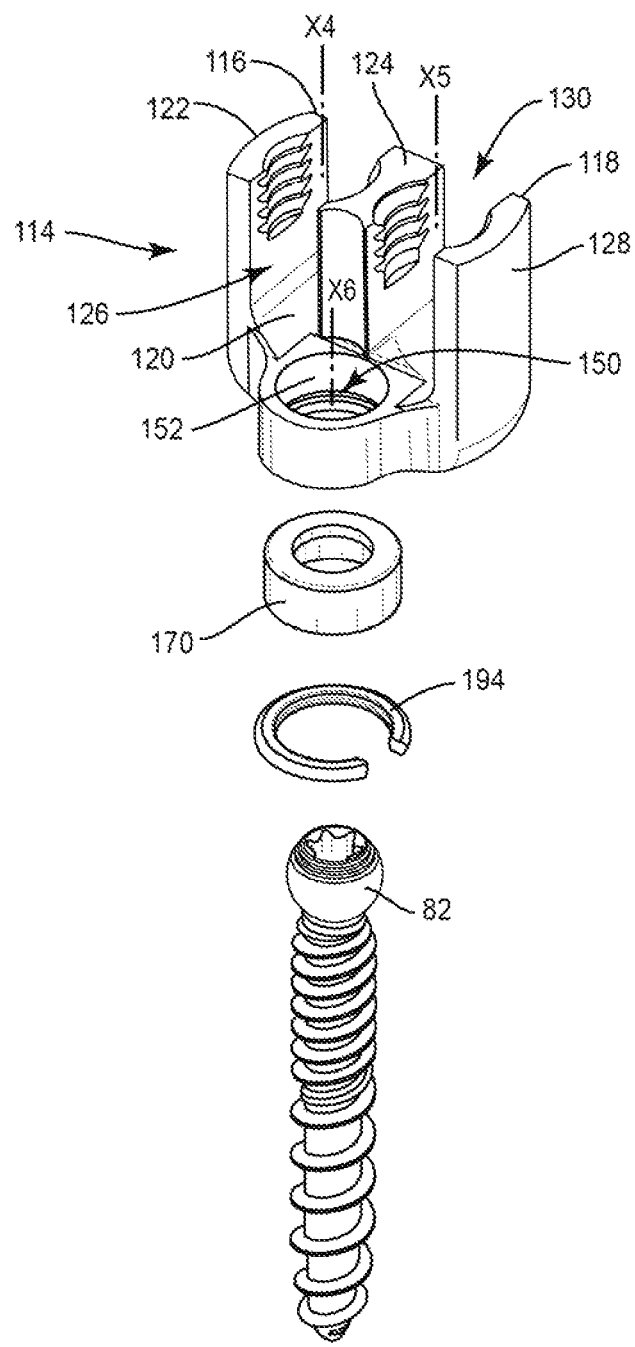
FIG. 6 is a perspective view of the components shown in FIG. 5 with parts separated.
Figure 7:
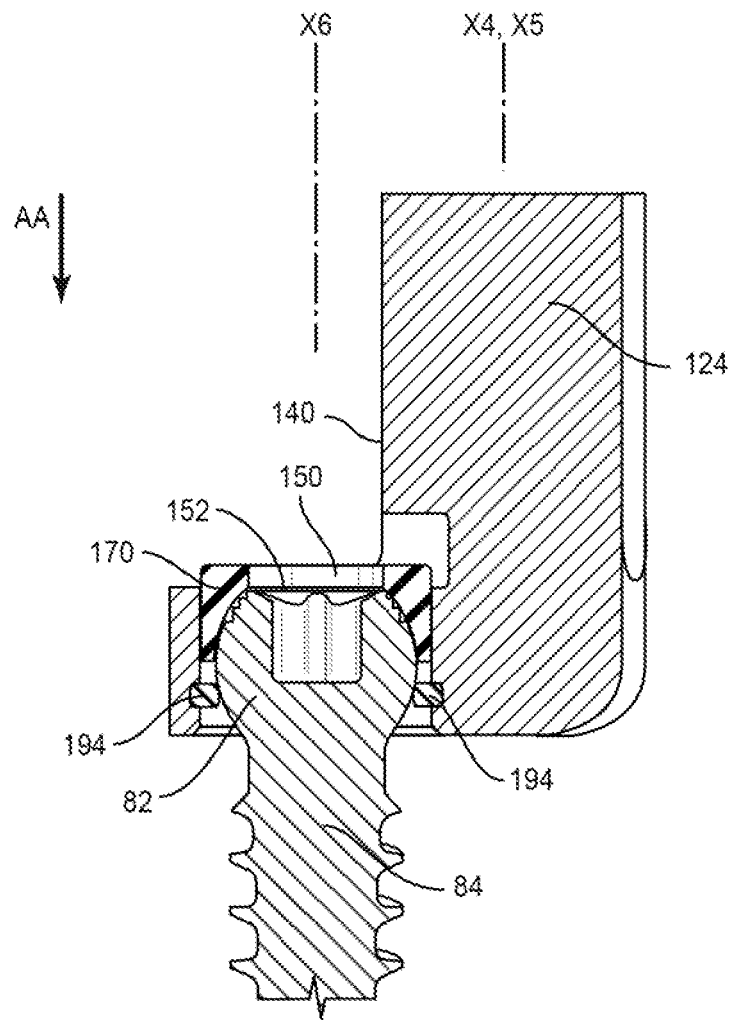
FIG. 7 is side cross section view of the components shown in FIG. 5.

In one embodiment, as shown in FIGS. 5-7, spinal implant system 10, similar to the systems and methods described herein, comprises a bone fastener 112, similar to bone fastener 12 described herein. Fastener 112 includes a receiver 114, similar to receiver 14 described herein, having an end 116 and an end 118. Receiver 114 includes a surface 120 that extends between ends 116, 118.

End 116 includes an arm 122 and a wall surface 123 of a medial arm 124 of receiver 114. Arm 122 and wall surface 123 are spaced apart to define a U-shaped implant cavity 126 therebetween, which is configured for disposal of a spinal implant, as described herein. Cavity 126 defines an axis X4. End 116 includes an inner surface 134, which comprises a portion of arm 122 and wall surface 123. Surface 134 includes a thread form 136 disposed along a portion of arm 122 and wall surface 123. Thread form 136 is configured for engagement with a coupling member, such as, for example, a setscrew (not shown) to retain a spinal rod within cavity 126.

End 118 includes an arm 128 and a wall surface 125 of arm 124. Arm 128 and wall surface 125 are spaced apart to define a U-shaped implant cavity 130 therebetween, which is configured for disposal of a spinal implant. Cavity 130 defines an axis X5 extending parallel to axis X4. Cavity 130 is disposed in spaced apart relation and adjacent cavity 122. End 118 includes an inner surface 138, which comprises a portion of arm 128 and wall surface 125. Surface 138 includes a thread form 140 disposed along a portion of arm 128 and wall surface 125. Thread form 140 is configured for engagement with a coupling member, such as, for example, a setscrew (not shown) to retain a spinal rod within cavity 130.

Surface 120 includes an inner surface 152 that defines a medial cavity such as, for example, an elongated axial passageway 150, similar to passageway 50 described herein. Passageway 150 is sized for passage of a surgical tool and/or for access to screw 80, as described herein. Passageway 150 defines a medial axis X6. Axis X6 is disposed in an offset orientation relative to axes X4, X5.

A part, such as, for example, an insert 170 is configured for disposal in passageway 150. Insert 170 includes a flange 172. Insert 170 communicates with cavity 126 and cavity 130 such that flange 172 is engageable with spinal implants disposed therein. In some embodiments, all or only a portion of flange 172 may have alternate surface configurations such as, for example, rough, arcuate, undulating, mesh, porous, semi-porous, dimpled and/or textured.

Insert 170 defines a central opening 174 aligned with passageway 150 for passage of a surgical tool and/or for access to screw 80, as described herein. In some embodiments, insert 170 is configured to fix a selected orientation of screw 80 relative to receiver 114, as described herein.

In some embodiments, flange 172 can include a flexible configuration. In some embodiments, all or only a portion of flange 172 may have a semi-rigid, rigid, flexible or elastic configuration, and/or have elastic and/or flexible properties such as the elastic and/or flexible properties of the material examples described above. As such, flange 172 can provide a selective amount of deformation in an axial direction to engage screw 80, as described herein. In some embodiments, flange 172 may be compressible in an axial direction.

Head 82 of screw 80 is configured for attachment to receiver 114 via a crown assembly, which includes insert 170 and a retainer ring 194. Insert 170 is aligned with passageway 150 and ring 194 mates with surface 152. Head 82 is disposed in a contacting engagement with an inner concave surface of insert 170. The outer surface of head 82 is engageable with the inner surface of insert 170 to facilitate fixation of shaft 84 in a selected orientation of screw 80 relative to receiver 114. In some embodiments, all or only a portion of the outer surface of head 82 and/or the inner surface of insert 170 may have alternate surface configurations to enhance fixation of the surfaces, such as, for example, rough, arcuate, undulating, mesh, porous, semi-porous, dimpled and/or textured.

Retainer ring 194 is configured for disposal about head 82 to assemble screw 80 and the crown assembly with receiver 114. Retainer ring 194 is engaged with an inner groove of surface 152. Retainer ring 194 captures head 82 to movably fix screw 80 with receiver 114. As such, screw 80 is moveable relative to receiver 114 in a multi-axial configuration and shaft 84 is selectively movable relative to receiver 114 and/or axis X6 through an angular range and disposable at a selected angle relative to receiver 114 and/or axis X6.

Insert 170 is configured to fix a selected orientation of screw 80, similar to insert 70 described herein, relative to receiver 114. In some embodiments, implants, such as, for example, spinal rods contact flange 172 such that an axial force is applied to flange 172, as shown by arrow AA in FIG. 7. Insert 170 is driven and translates, in the direction shown by arrow AA, into engagement with head 82 and/or retainer ring 194. As such, the axial force is applied to one or more components of the crown assembly to fix a selected orientation of screw 80 relative to receiver 114, as described herein.

Figure 8:
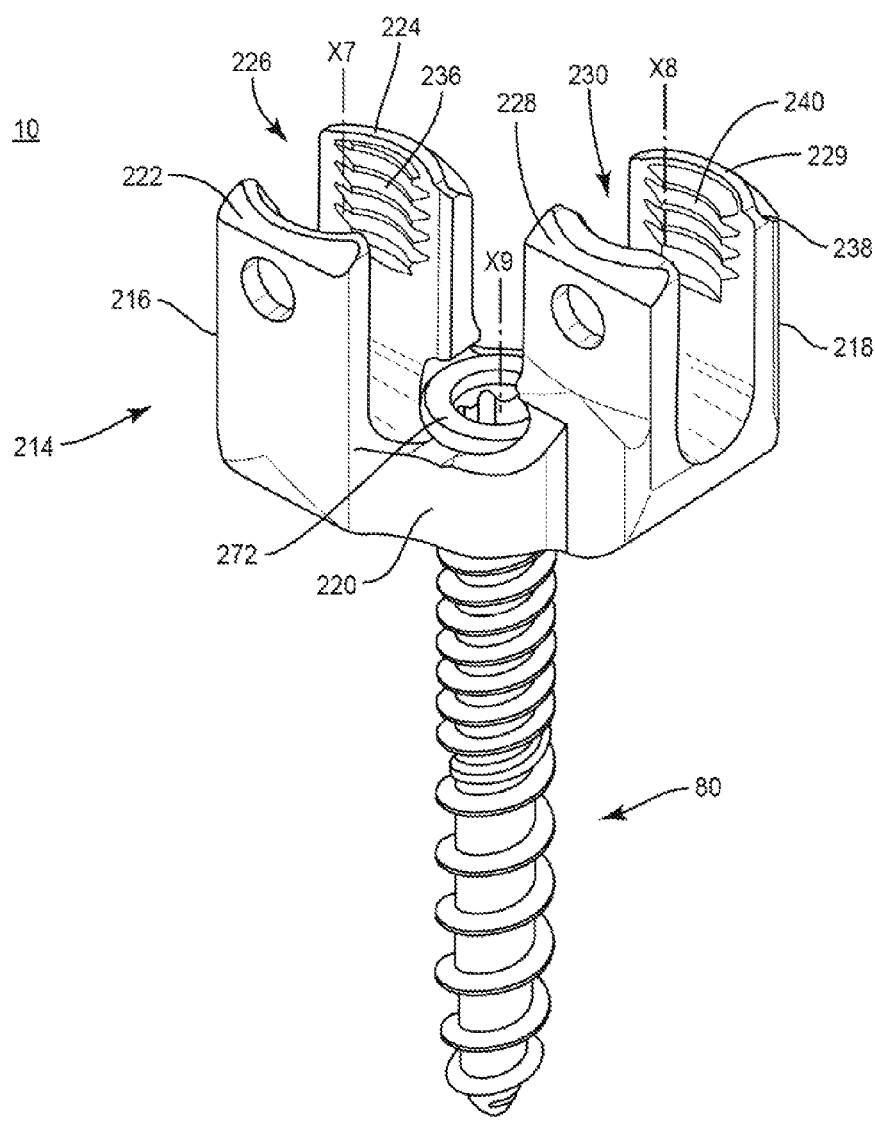
FIG. 8 is a perspective view of components of one embodiment of a spinal implant system in accordance with the principles of the present disclosure.
Figure 9:
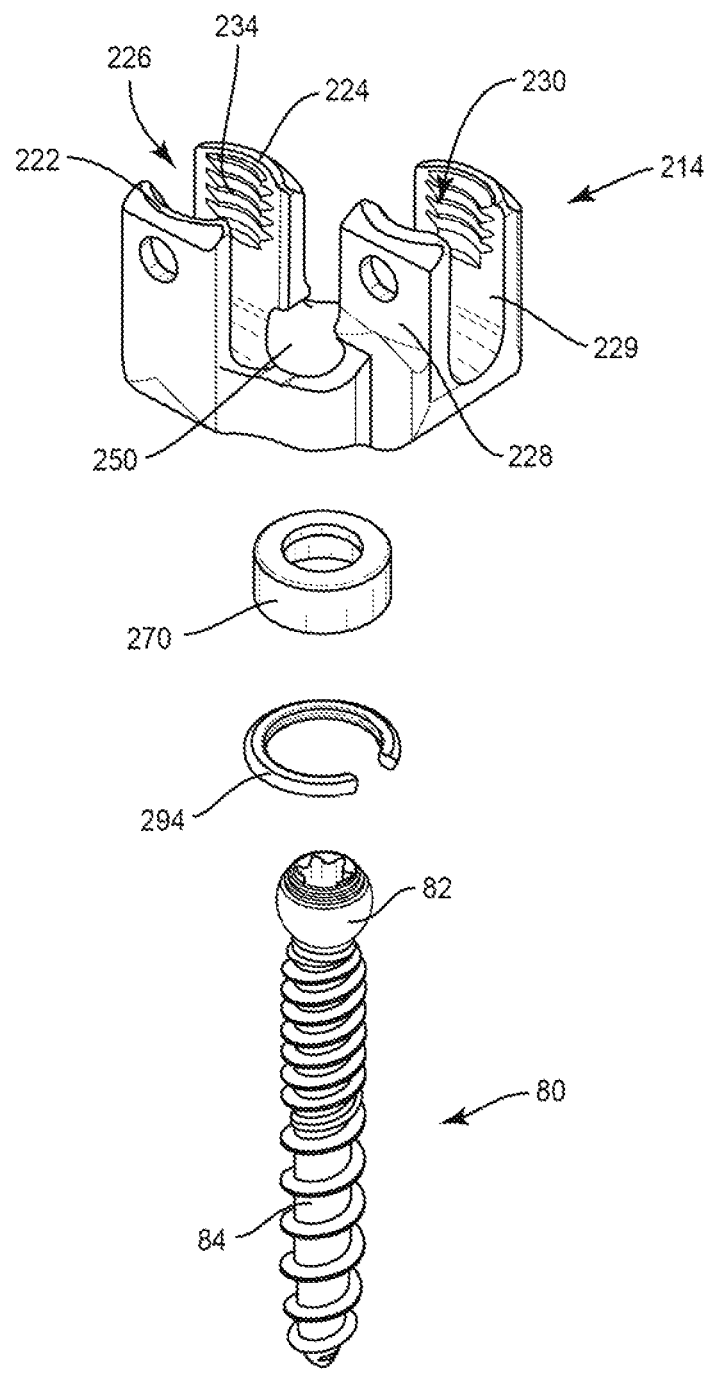
FIG. 9 is a perspective view of the components shown in FIG. 8 with parts separated.
Figure 10:
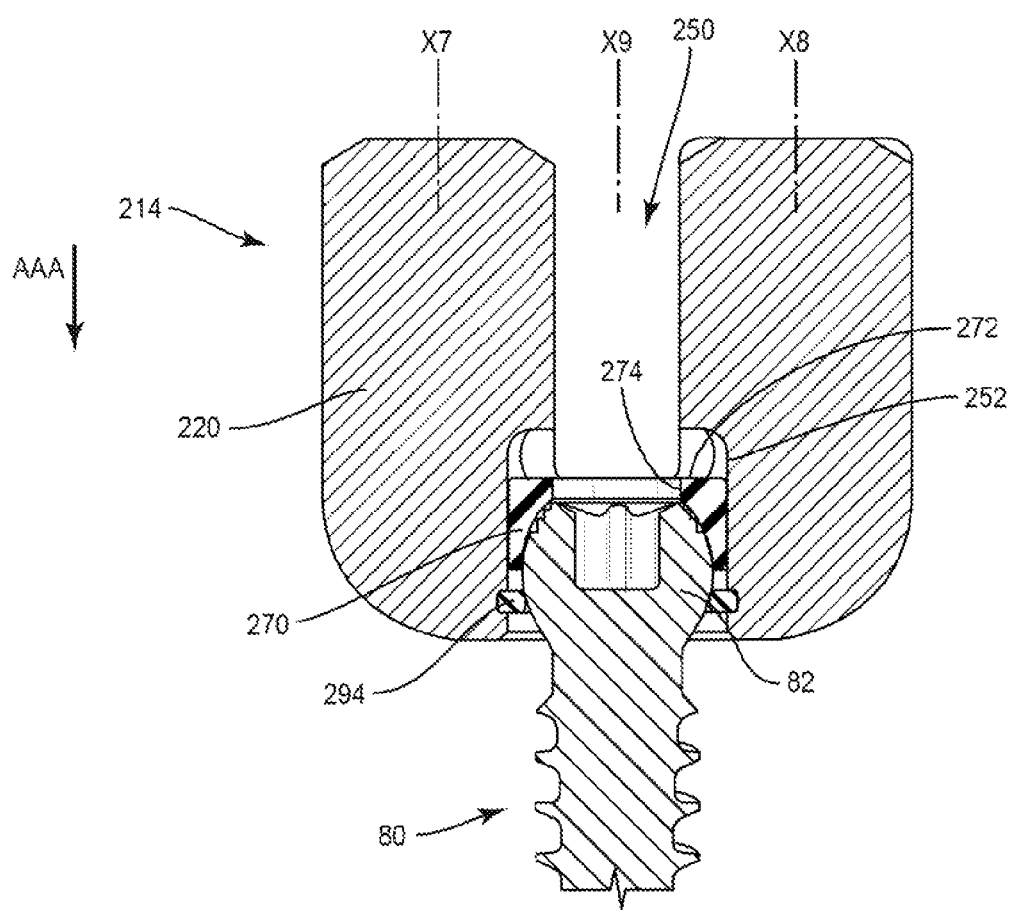
FIG. 10 is cross section view of the components shown in FIG. 8.

In one embodiment, as shown in FIGS. 8-10, spinal implant system 10, similar to the systems and methods described herein, comprises a bone fastener 212, similar to bone fastener 12 described herein. Fastener 212 includes a receiver 214, similar to receiver 14 described herein, having an end 216 and an end 218. Receiver 214 includes a surface 220 that extends between ends 216, 218.

End 216 includes an arm 222 and an arm 224 that are spaced apart to define a U-shaped implant cavity 226 therebetween, which is configured for disposal of a spinal implant, as described herein. Cavity 226 defines an axis X7. End 216 includes an inner surface 234, which includes a thread form 236. Thread form 236 is configured for engagement with a coupling member, such as, for example, a setscrew (not shown) to retain a spinal rod within cavity 226.

End 218 includes an arm 228 and an arm 229 that are spaced apart to define a U-shaped implant cavity 230 therebetween, which is configured for disposal of a spinal implant. Cavity 230 defines an axis X8 extending parallel to axis X7. Cavity 230 is disposed in spaced apart relation and adjacent cavity 226. End 218 includes an inner surface 238, which includes a thread form 240. Thread form 240 is configured for engagement with a coupling member, such as, for example, a setscrew (not shown) to retain a spinal rod within cavity 230.

Surface 220 includes an inner surface 252 that defines a medial cavity such as, for example, an axial passageway 250, similar to passageway 50 described herein. Passageway 250 is sized for passage of a surgical tool and/or for access to screw 80, as described herein. Passageway 250 defines a central axis X9. In some embodiments, axes X7, X8, X9 are relatively disposed in a staggered orientation. In some embodiments, axes X7, X8, X9 are relatively disposed in a staggered orientation such that axes X7, X8, X9 are disposed along a common diagonal. In some embodiments, axis X7 is offset from axis X9 and axis X8 is offset from axis X9.

A part, such as, for example, an insert 270 is configured for disposal in passageway 250. Insert 270 includes a flange 272. Insert 270 communicates with cavity 226 and cavity 230 such that flange 272 is engageable with spinal implants disposed therein. In some embodiments, all or only a portion of flange 272 may have alternate surface configurations such as, for example, rough, arcuate, undulating, mesh, porous, semi-porous, dimpled and/or textured.

Insert 270 defines a central opening 274 aligned with passageway 250 for passage of a surgical tool and/or for access to screw 80, as described herein. In some embodiments, insert 270 is configured to fix a selected orientation of screw 80 relative to receiver 214, as described herein.

In some embodiments, flange 272 can include a flexible configuration. In some embodiments, all or only a portion of flange 272 may have a semi-rigid, rigid, flexible or elastic configuration, and/or have elastic and/or flexible properties such as the elastic and/or flexible properties of the material examples described above. As such, flange 272 can provide a selective amount of deformation in an axial direction to engage screw 80, as described herein. In some embodiments, flange 272 may be compressible in an axial direction.

Head 82 of screw 80 is configured for attachment to receiver 214 via a crown assembly, which includes insert 270 and a retainer ring 294. Insert 270 is aligned with passageway 250 and ring 294 mates with surface 252. Head 82 is disposed in a contacting engagement with an inner concave surface of insert 270. The outer surface of head 82 is engageable with the inner surface of insert 270 to facilitate fixation of shaft 84 in a selected orientation of screw 80 relative to receiver 214. In some embodiments, all or only a portion of the outer surface of head 82 and/or the inner surface of insert 270 may have alternate surface configurations to enhance fixation of the surfaces, such as, for example, rough, arcuate, undulating, mesh, porous, semi-porous, dimpled and/or textured.

Retainer ring 294 is configured for disposal about head 82 to assemble screw 80 and the crown assembly with receiver 214. Retainer ring 294 is engaged with an inner groove of surface 252. Retainer ring 294 captures head 82 to movably fix screw 80 with receiver 214. As such, screw 80 is moveable relative to receiver 214 in a multi-axial configuration and shaft 84 is selectively movable relative to receiver 214 and/or axis X9 through an angular range and disposable at a selected angle relative to receiver 214 and/or axis X9.

Insert 270 is configured to fix a selected orientation of screw 80, similar to insert 70 described herein, relative to receiver 214. In some embodiments, implants, such as, for example, spinal rods contact flange 272 such that an axial force is applied to flange 272, as shown by arrow AAA in FIG. 10. Insert 270 is driven and translates, in the direction shown by arrow AAA, into engagement with head 82 and/or retainer ring 294. As such, the axial force is applied to one or more components of the crown assembly to fix a selected orientation of screw 80 relative to receiver 214, as described herein.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant comprising:
a first member including a surface that extends between a first portion and a second portion, the first member defining a first implant cavity adjacent the first portion and a second implant cavity adjacent the second portion, the implant cavities each extending through a top surface of the first member, the first implant cavity being spaced from the second implant cavity by a wall that includes threaded wall surfaces, the wall defining a medial cavity between the wall surfaces, the first member including an aperture that extends through a bottom surface of the first member such that the aperture is aligned with the medial cavity;
a retainer positioned within the aperture, the retainer comprising an outer thread form that is engaged with an inner thread form of the first member;
a crown movably positioned within the retainer; and
a second member being movable relative to the first member, the second member including a first end that directly engages the crown and a second end configured to penetrate tissue.

2. A spinal implant as recited in claim 1, wherein the second member is movable along a plurality of axes relative to the first member.

3. A spinal implant as recited in claim 1, wherein the first end includes a head defining a socket engageable with a surgical driver via the medial cavity.

4. A spinal implant as recited in claim 1, wherein the first member defines a central axis, the medial cavity being disposed along the central axis.

5. A spinal implant as recited in claim 1, wherein the first member defines a central axis, the first implant cavity defines a first axis and the second implant cavity defines a second axis, the central axis being disposed in a parallel orientation relative to the first axis and the second axis.

6. A spinal implant as recited in claim 1, wherein the medial cavity comprises an elongated passageway centrally disposed with the first member.

7. A spinal implant as recited in claim 1, wherein the aperture is in communication with the medial cavity and is offset relative to the first implant cavity and the second implant cavity.

8. A spinal implant as recited in claim 1, wherein a first arm of the first member, a second arm of the first member and the wall surfaces define the implant cavities.

9. A spinal implant as recited in claim 1, further comprising a part disposed in at least one of the first implant cavity and the second implant cavity such that the crown is mated with the part, the part being engageable with a longitudinal element to fix a selected orientation of the second member relative to the first member.

10. A spinal implant as recited in claim 9, wherein the part extends through the first member for disposal in the first implant cavity and the second implant cavity.

11. A spinal implant as recited in claim 9, wherein the crown comprises a lip that is positioned within in an opening of the part, the part being engageable with the crown to fix the selected orientation.

12. A spinal implant as recited in claim 1, wherein the first member includes a plurality of arms that define the implant cavities, at least one of the arms including an overlap to maintain the crown with the first end.

13. A spinal implant as recited in claim 1, wherein the first member comprises a passageway that extends perpendicular to the implant cavities, the spinal implant comprising an insert positioned within the passageway such that a first part of the insert is disposed in the first implant cavity and a second part of the insert is disposed in the second implant cavity, the crown having a lip that extends through an opening of the insert, the insert being engageable with a longitudinal element to fix a selected orientation of the second member relative to the first member.

14. A spinal implant as recited in claim 13, wherein the opening of the insert is aligned with the medial cavity and the aperture.

15. A spinal implant as recited in claim 1, wherein a convex surface of the first end directly engages an inner concave surface of the crown.

16. A bone fastener comprising:
    a first member including arms that define portions of a first implant receiver and a second implant receiver that is spaced apart from the first implant cavity by a wall having threaded wall surfaces, the wall defining a central passageway between the wall surfaces, the first member including an aperture that is aligned with the central passageway;
    a retainer positioned within the aperture, the retainer comprising an outer thread form that is engaged with an inner thread form of the first member;
    a crown movably positioned within the retainer;
    a part extending through the first member and disposable with the receivers; and
    a screw movable along a plurality of axes relative to the first member, the screw including a head that directly engages the crown and a threaded shaft configured to penetrate tissue.

17. A bone fastener as recited in claim 16, wherein the head defines a socket engageable with a surgical driver via the central passageway.

18. A bone fastener as recited in claim 16, wherein the first implant receiver defines a first axis and the second implant receiver defines a second axis, the central passageway being disposed in a parallel orientation relative to the first axis and the second axis.

19. A bone fastener as recited in claim 16, wherein the part is engageable with the crown, a longitudinal element disposed with the first implant receiver and a longitudinal element disposed with the second implant receiver to fix a selected orientation of the screw relative to the first member.

20. A spinal implant system comprising:
    a bone fastener comprising a first member including a surface that extends between a first portion and a second portion, the first member defining a first cavity adjacent the first portion and a second cavity adjacent the second portion, the surface defining a medial cavity, the first member including an aperture that is aligned with the medial cavity,
    a retainer positioned within the aperture, the retainer comprising an outer thread form that is engaged with an inner thread form of the first member,
    a crown movably positioned within the retainer,
    a part extending through the first member and disposed with the first and second cavities, the part comprising an outer surface that directly engages an outer surface of the crown and an opening that is aligned with the medial cavity, the crown comprising a lip that is disposed in the opening, and
    a second member being movable relative to the first member, the second member including a first end aligned with the medial cavity and a second end configured to penetrate tissue, the first end including a spherical head that directly engages an inner concave surface of the crown;
    a first spinal rod disposed with the first cavity; and
    a second spinal rod disposed with the second cavity,
    wherein the rods are engageable to fix a selected orientation of the second member relative to the first member.

* * * * *

UNITED STATES PATENT AND TRADEMARK OFFICE
CERTIFICATE OF CORRECTION

PATENT NO. : 9,949,763 B2
APPLICATION NO. : 14/303836
DATED : April 24, 2018
INVENTOR(S) : Rezach It is certified that error appears in the above-identified patent and that said Letters Patent is hereby corrected as shown below:

In Column 3, Line 33, delete ""about"" and insert -- "about," --, therefor.

In Column 5, Line 36, delete "cavity 22." and insert -- cavity 26. --, therefor.

In Column 8, Line 33, delete "thread forms 36, 38" and insert -- thread forms 36, 40 --, therefor.

In Column 8, Lines 44-45, delete "spinal correction system" and insert -- spinal implant system --, therefor.

In Column 8, Line 47, delete "25a. 25b" and insert -- 25a, 25b --, therefor.

In Column 8, Line 52, delete "similarity" and insert -- similarly --, therefor.

In Column 9, Line 47, delete "cavity 122." and insert -- cavity 126. --, therefor.

In Column 13, Line 5, in Claim 11, delete "within in an" and insert -- within an --, therefor.

Signed and Sealed this
Fourth Day of December, 2018

Andrei Iancu
*Director of the United States Patent and Trademark Office*